United States Patent [19]

Radecki

[11] Patent Number: 5,140,032

[45] Date of Patent: Aug. 18, 1992

[54] DRUG THERAPY FOR ALCOHOL ABUSERS

[76] Inventor: Thomas E. Radecki, 1600 Lincoln, Decatur, Ill. 62521

[21] Appl. No.: 591,684

[22] Filed: Oct. 1, 1990

[51] Int. Cl.$^5$ .................... A61K 31/55; A61K 31/27
[52] U.S. Cl. .................................. 514/221; 514/491; 514/811
[58] Field of Search ................ 514/811, 599, 221, 491

[56] References Cited

PUBLICATIONS

"Engaging the Alcoholic in Treatment and Keeping Him There", Chapter 4, Frederick Baekeland and Lawrence K. Lundwall, pp. 161–195 (1977).

"Lack of interaction between disulfiram and alprazolam in alcoholic patients", Eur J Clin Pharmacol (1990) 38:157–160, B. Diquet et al.

"Interaction of disulfiram with benzodiazepines", Clin. Pharmacol. Ther. Nov. 1978, S. M. MacLeod et al., pp. 583–589.

"A Bahavioral Treatment of Alcoholic Methadone Patients", Ira A. Liebson et al., Annals of Internal Medicine 89:342–344, 1978.

Sellers et al.: New England J Medicine 305(21):1255–1262 1981.

Peachey et al.: Drugs 27(2):171–182 1984.

Kissin: Ann N.Y. Acad Science 252:385–395 1975.

Peachy et al.: Psychiatric Clinics of N. America 7(4):745–756 1984.

Preskorn et al.: Int'l Journal Psychiatry in Medicine 17(2):117–131 1987.

Sellers et al.: Arzneim.-Forsch/Drug Res. 30(I) Nr (5A):882–886 1980.

MacLeod et al.: Clinical Pharmacol. Ther. 24(5):583–589 1978.

Primary Examiner—Frederick E. Waddell
Assistant Examiner—Diane Gardner
Attorney, Agent, or Firm—Hill, Van Santen, Steadman & Simpson

[57] ABSTRACT

A novel composition and/or method for the treatment of alcoholism, wherein the composition comprises a therapeutically effective dosage of disulfiram and a drug that affects the neurological system in a manner similar to alcohol, preferably a habit-forming or addictive drug. The method comprises administering a composition to alcoholics that combines therapeutically effective dosages of disulfiram and a habit-forming or addictive drug into a single composition. Preferably, the habit-forming or addictive medication is an anti-anxiety drug and is a member of the benzodiazepine family. Most preferably, the habit-forming, anti-anxiety drug is diazepam.

48 Claims, No Drawings

DRUG THERAPY FOR ALCOHOL ABUSERS

BACKGROUND OF THE INVENTION

The present invention relates to a method and composition for the treatment of alcoholism. More specifically, the present invention relates to a method that utilizes a composition comprised of two medications to treat alcohol abuse and improve patient compliance with treatment programs.

Alcoholism is a severe disease. The deaths of over 105,000 Americans each year and over one million persons worldwide are attributed to this disease. Despite the existence of a variety of treatment programs, success rates for treating alcoholism are relatively low, usually in the 20% to 30% range after one year of abstinence. Yet, even these figures may underestimate the difficulty of treating alcoholism, since many individuals are unwilling to enter into any alcohol treatment program.

The typical treatment of alcoholism has sometimes involved the use of drug therapy. Disulfiram, also known as Antabuse, has been widely used since the early 1950's in the treatment of alcoholism. Disulfiram causes a strong adverse reaction in a person within five to fifteen minutes after the person has consumed alcohol. Side-effects are believed to be minimal, and life-threatening reactions with or without alcohol are very rare. Unfortunately, disulfiram therapy has resulted in only modest success in treating alcoholism. In a recent large scale, multi-center study by the Veterans Administration (VA), the one-year abstinence rate for patients on disulfiram (18%) was no better than for the control group (20%), but disulfiram patients had significantly more days of sobriety. Typically, patients cease taking the disulfiram and discontinue treatment, resulting in a relapse in alcohol abuse.

One drug that is commonly used for alcohol detoxification, but not for therapy, is diazepam, a member of the benzodiazepine family of somewhat habit-forming, anti-anxiety medications. Diazepam appears to decrease cravings for alcohol. A significant disadvantage, however, with using diazepam is that alcoholics, after only a short period of time, frequently relapse into drinking while continuing to take diazepam. Further treatment of the alcohol abuse is subsequently discontinued.

Although initially effective, existing pharmacological therapies fail to provide adequate treatment for long-term and severe alcohol abuse. Accordingly, an alternative approach for the treatment of alcoholics would be useful in improving abstinence from alcohol.

SUMMARY OF THE INVENTION

The present invention provides a novel and effective composition and/or method for treating alcoholism. To this end, the present invention utilizes a method that combines therapeutically effective dosages of two medications, disulfiram and a drug that affects the neurological system in a manner similar to alcohol, such as diazepam, into a single composition. The single composition can be administered to alcoholics following a brief (usually 12 hour) period of detoxification so as to maintain abstinence from alcohol. Use of the combined medication by alcoholics can significantly improved abstinence from alcohol and result in greater compliance with the treatment program.

In an embodiment of the present invention, the present invention provides a method of treating alcoholics following a period of detoxification. The method preferably comprises the steps of administering a composition to an alcoholic comprising a therapeutically effective dosage of disulfiram and a benzodiazepine or similar minor tranquilizer or additive, anti-anxiety medication.

In one embodiment of the composition of the present invention, the dosage comprises 125 mg of disulfiram and 10 mg of diazepam.

Additional features and advantages of the present invention are further disclosed and will be apparent from the detailed description of the presently preferred embodiments and accompanying drawings.

DETAILED DESCRIPTION OF THE PRESENTLY PREFERRED EMBODIMENTS

The present invention provides a new treatment for alcoholism, wherein therapeutically effective dosages of disulfiram and a benzodiazepine or related minor tranquilizer or addictive, medication are combined in a single composition for ingestion by alcoholics. Initial studies indicate that, after repeatedly failing other therapeutic approaches, alcoholics that take the combination medication, show significant improvement in abstinence from alcohol and remain in therapy. The marked improvement is attributed to the qualities of the combination medication, which are not evident when each medication is administered separately. The reinforcing quality of a benzodiazepine medication such as diazepam results in greater compliance by the alcoholics with the treatment program, i.e., the taking of the composition. But equally as important and vitally necessary, the addition of disulfiram prevents relapse into alcohol abuse.

By way of example, and not limitation, the following examples serve to further illustrate the present invention in its preferred embodiments.

EXAMPLE 1 - Clinical Studies

Studies were conducted on six patients whose long-term alcohol abuse persisted despite multiple hospitalizations and participation in 28-day treatment programs. Because the combination medication was initially unavailable, the patients were given separate pills of disulfiram and diazepam. Approximately 125 mg of disulfiram and 10 mg of diazepam were administered once or twice a day to each patient.

Within one week, four of the six patients ceased taking the disulfiram. Although they continued taking the diazepam, the patients relapsed into alcohol abuse. Drinking continued while taking the diazepam, thereby creating additional risks for the patients. The fifth patient was given the pills each day by a parent, and the sixth did maintain sobriety.

Subsequently, the four patients who ceased taking the disulfiram were treated with the combination medication of the present invention comprising a single tablet containing 125 mg of disulfiram and 10 mg of diazepam, given twice daily. Preliminary results indicate that treatment with the combination medication is markedly better than the treatment with the medications individually. Improvement in sobriety and compliance with therapy was seen in these patients receiving the combination medication. These patients continued to abstain from alcohol abuse and currently remain in therapy, results which none had previously achieved with other treatment approaches. Further, there appears to be no adverse reaction with the use of the combination medication, other than minor side-effects which can be alleviated with simple adjustments.

These results suggest that alcoholics benefit from qualities of the combination medications not present in the two medications, when administered separately. Specifically, the reinforcing quality of diazepam appears to facilitate patient compliance in continuing the treatment program, while the disulfiram prevents a relapse into alcohol abuse. In one sense, a patient becomes mildly addicted or "hooked" to the medication by being addicted to the diazepam or other habit-forming drug. However, this addiction is quite easily managed by gradual withdrawal after the alcoholic has achieved sobriety and made lifestyle changes. The mild addiction actually benefits the treatment's success.

EXAMPLE 2 - Treatment Dosages and Program

The disulfiram-diazepam treatment consists of administering to the average patient a combination capsule or pill containing a standard starting dosage of 125 mg of disulfiram and 10 mg of diazepam. The starting dose should be given twice a day with a maximum of four times a day. If given only twice a day, the dosage should be supplemented by the addition of 250 mg of disulfiram once a day, so that the total disulfiram dosage for the first two weeks is a standard 500 mg. After the first two weeks, the recommended dosage of disulfiram is 250 mg daily or the equivalent of two combination capsules or pills per day.

Dosage preparations of 125 mg of disulfiram combined with either 2 mg or 5 mg of diazepam are recommended for patients who are susceptible to the sedative effects of diazepam. Further, after patients have achieved extended abstinence and stability for a three month to two year period, these weaker preparations should be used in weaning patients off of diazepam.

Ideally, the disulfiram-diazepam combination should be administered in conjunction with a comprehensive treatment program, including group and individual therapy and often brief hospitalization or in-patient residential treatment.

It is contemplated that in addition to diazepam, other medications including sedatives (e.g., chloral hydrate) and pain medications (e.g., Darvon®) could be used. However, it is likely that the most effective medications are those that are similar to alcohol in their effects on the patient's neurological system.

Further, although to date only capsules of the combination medication have been used, it is contemplated that the medication can be bound in tablet form.

The present invention involves the various embodiments associated with the combination of disulfiram and a habit-forming or addictive, anti-anxiety drug, such as diazepam, in a single composition and its use in all respects, and is not to be construed as limited to any specific aspect or embodiment except as defined by the lawful scope of the appended claims.

I claim:

1. A method of treating alcoholism comprising the step of:
   administering a composition to an alcoholic, said composition consisting of a therapeutically effective dosage of disulfiram and a medication that is similar to alcohol in its affect on the neurological system of the alcoholic.

2. The method of claim 1, wherein said medication is selected from the group consisting of: sedatives, pain medications, and addictive, anti-anxiety medications.

3. The method of claim 1, wherein said medication is habit-forming.

4. The method of claim 3, wherein said habit-forming medication is an anti-anxiety drug.

5. The method of claim 4, wherein said habit-forming medication is a benzodiazepine-related compound.

6. The method of claim 5, wherein said benzodiazepine-related compound is diazepam.

7. The method of claim 1, wherein said composition is bound in an encapsulated form.

8. The method of claim 1, wherein said composition is bound in a tablet form.

9. The method of claim 1, wherein said composition includes 125 mg of disulfiram.

10. The method of claim 1, wherein said composition includes 10 mg of diazepam.

11. The method of claim 1, wherein the step of administering said composition is undertaken two to four times a day.

12. A method of treating an alcoholic patient following a period of detoxification to encourage abstinence from alcohol, comprising the steps of:
   providing the alcoholic patient with a therapeutically effective composition of disulfiram and a medication that is similar to alcohol in its effect on the neurological system; and
   reinforcing the alcoholic patient to comply with treatment by the presence of a medication that is similar to alcohol in its affect on the neurological system, whereby the patient desires to ingest the disulfiram and the medication simultaneously.

13. The method of claim 12, wherein said medication is selected from the group consisting of: sedatives, pain medications, and addictive, anti-anxiety medications.

14. The method of claim 12, wherein said medication is habit-forming.

15. The method of claim 14, wherein said habit-forming medication is an anti-anxiety drug.

16. The method of claim 15, wherein said habit-forming medication is a benzodiazepine-related compound.

17. The method of claim 16, wherein said benzodiazepine-related compound is diazepam.

18. The method of claim 12, wherein said composition is bound in an encapsulated form.

19. The method of claim 12, wherein said composition is bound in a pill form.

20. The method of claim 12, wherein said composition includes 125 mg of disulfiram.

21. The method of claim 12, wherein said composition includes 10 mg of diazepam.

22. The method of claim 12, wherein the step of administering said composition is undertaken two to four times a day.

23. A composition for treating alcoholism comprising:
   a therapeutically effective dosage of disulfiram and a medication that is similar to alcohol in its affect on the neurological system.

24. The composition of claim 23, wherein said medication is selected from the group of depressants consisting of: sedatives, pain medications, and addictive, anti-anxiety medications.

25. The composition of claim 23, wherein said medication is habit-forming.

26. The composition of claim 25, wherein said habit-forming medication is an anti-anxiety drug.

27. The composition of claim 26, wherein said habit-forming medication is a benzodiazepine-related compound.

28. The composition of claim 27, wherein said benzodiazepine-related compound is diazepam.

29. The composition of claim 23, wherein said composition is bound in an encapsulated form.

30. The composition of claim 23, wherein said composition is bound in a pill form.

31. The composition of claim 23, wherein said composition includes 125 mg of disulfiram.

32. The composition of claim 23, wherein said composition includes 10 mg of diazepam.

33. A composition for treatment of alcoholics after a period of sobriety and stability, said composition comprising a therapeutically effective dosage of disulfiram and a medication that is similar to alcohol in its affect on the neurological system.

34. The composition of claim 33, wherein said medication is selected from the group of depressants consisting of: sedatives, pain medications and additives, anxiety medications.

35. The composition of claim 33, wherein said medication is habit-forming.

36. The composition of claim 35, wherein said habit-forming medication is an anti-anxiety drug.

37. The composition of claim 36, wherein said habit-forming medication is a benzodiazepine-related compound.

38. The composition of claim 37, wherein said benzodiazepine-related compound is diazepam.

39. The composition of claim 33, wherein said composition is bound in an encapsulated form.

40. The composition of claim 33, wherein said composition is bound in a pill form.

41. The composition of claim 33, wherein said composition includes 125 mg of disulfiram and between 2 mg and 5 mg of diazepam.

42. A composition for inducing alcohol abstinence in a detoxified alcoholic, comprising:
    disulfiram and a medication that is similar to alcohol in its affect on the neurological system.

43. The composition of claim 42, wherein said medication is selected from the group of depressants consisting of: sedatives, pain-medications, and addictive, anti-anxiety medications.

44. The composition of claim 42, wherein said medication is habit-forming.

45. The composition of claim 44, wherein said habit-forming medication is an anti-anxiety drug.

46. The composition of claim 44, wherein said habit-forming medication is a benzodiazepine-related compound.

47. The composition of claim 46, wherein said benzodiazepine-related compound is diazepam.

48. The composition of claim 42, wherein said composition includes 125 mg of disulfiram and 10 mg of diazepam.

* * * * *